United States Patent

Heffelfinger et al.

[11] Patent Number: 5,897,760
[45] Date of Patent: Apr. 27, 1999

[54] METHOD AND APPARATUS FOR THE REMOVAL OF NON-UNIFORMITIES IN AN ELECTROPHORESIS APPARATUS

[75] Inventors: David M. Heffelfinger, San Pablo; Craig Van Horn, Sebastapol, both of Calif.

[73] Assignee: Bio-Rad Laboratories, Inc., Hercules, Calif.

[21] Appl. No.: 08/814,127

[22] Filed: Mar. 10, 1997

[51] Int. Cl.⁶ ................................................. G01N 27/26
[52] U.S. Cl. ........................ 204/612; 204/461; 356/344
[58] Field of Search .................................. 204/452, 612; 77/461, 603; 356/344

[56] References Cited

U.S. PATENT DOCUMENTS

| | | | |
|---|---|---|---|
| 4,737,464 | 4/1988 | McConnell et al. | 436/43 |
| 4,822,168 | 4/1989 | Nogami et al. | 356/319 |
| 4,874,492 | 10/1989 | Mackay | 204/461 |
| 5,294,323 | 3/1994 | Togusari et al. | 204/612 |
| 5,307,148 | 4/1994 | Kambara et al. | 356/344 |
| 5,672,881 | 9/1997 | Striepeke et al. | 250/461.2 |

FOREIGN PATENT DOCUMENTS

0241904 A2  10/1987  European Pat. Off. .

*Primary Examiner*—Robert Warden
*Assistant Examiner*—Alex Noguerda
*Attorney, Agent, or Firm*—David G. Beck; Townsend and Townsend and Crew

[57] ABSTRACT

A method and apparatus for correcting non-uniformities in the source and the lens assembly of an electrophoresis apparatus is provided. Assuming a detector with a uniform responsivity, correcting for source and lens non-uniformities allows quantitative measurements of an electrophoresis gel to be made, thus increasing the information which can be obtained from an electrophoretic analysis. The non-uniformities due to the illumination source are characterized by sampling a portion of the source with a linear detector array and creating a correction data file. In order to sample the source, a mirror or beamsplitter is appropriately positioned, for example along the central optical axis of the electrophoresis apparatus. Similarly, a correction data file representing the non-uniformities due to the lens assembly is created using a secondary linear source of known uniformity. After the correction data files are stored, an image of the sample is taken and a sample data file is created. The sample data file can be normalized using the correction data files thereby creating a corrected sample file which can either be displayed or stored for future use.

22 Claims, 7 Drawing Sheets

METHOD AND APPARATUS FOR THE REMOVAL OF NON-UNIFORMITIES IN AN ELECTROPHORESIS APPARATUS

The present invention relates generally to electrophoresis reading systems and, more particularly, to a method and apparatus for removing non-uniformities due to the illumination source and lens assembly from an electrophoresis system.

BACKGROUND OF THE INVENTION

In the biotechnical field, fluorescent dyes are routinely used as sensitive, non-isotopic labels. These labels are used to identify and locate a variety of cell structures, ranging from malignant tumors to specific chromosomes in a DNA sequence. A variety of devices have been designed to read fluorescent-labeled samples.

Gel electrophoresis is one technique commonly used in conjunction with fluorescent dyes and other markers to identify specific molecules as well as other tagged units. In this technique an electric field is used to cause the migration of the tagged units through a gel or other solution.

In U.S. Pat. No. 4,874,492 a gel electrophoresis system is disclosed in which samples are treated with fluorescent markers prior to applying them to an electrophoretic gel. The gel is illuminated with a UV source and the fluorescence pattern is detected with a cooled charge-coupled-device (CCD) two-dimensional detector array. The CCD array is cooled to at least −25 degrees C. in order to improve light sensitivity and increase the dynamic range.

In U.S. Pat. No. 5,162,654 a system is disclosed to optically determine which of four fluorophores is fluorescing in an electrophoresis gel. Fluorescence emitted by the gel passes first through four separate band pass filters and then through four wedge prisms. As a result of this optical configuration, the emitted fluorescence is imaged on four discrete areas on the detector array. The specific fluorophore exited by the irradiation source is determined by comparing the relative intensities of the fluorescence detected in the four detection areas.

In U.S. Pat. No. 5,294,323 the disclosed gel electrophoresis system utilizes a vertical electrophoresis plate. A laser beam passes horizontally through the gel in a direction perpendicular to the longitudinal axis of the electrophoresis plate. The emitted fluorescence is reflected to a solid state imaging sensor such that the reflected pattern is parallel to the direction of the laser beam.

In U.S. Pat. No. 5,324,401 a fluorescence detection system for capillary electrophoresis is disclosed which provides for the simultaneous excitation and detection of fluorescent probes within a plurality of capillaries. The excitation source is a laser which is coupled to the capillaries through an optical fiber bundle. The fluorescence from the capillary array is focussed through a lens and imaged onto a CCD camera for analysis.

In a paper by Sutherland et al. entitled "Electronic Imaging System for Direct and Rapid Quantitation of Fluorescence from Electrophoretic Gels: Application to Ethidium Bromide-Stained DNA" published in *Analytical Biochemistry* 163, 446–457 (1987), the authors describe an imaging system which uses a CCD camera. The CCD camera quantifies the fluorescence received from electrophoretic gels, chromatograms, and other sources. The paper describes several sources of non-uniformities which impact the ability of the system to obtain accurate results.

From the foregoing, it is apparent that an improved electrophoresis apparatus is desired which enables accurate quantitative fluorescence measurements.

SUMMARY OF THE INVENTION

The present invention provides a method and apparatus for correcting for the non-uniformities in an electrophoresis apparatus. These non-uniformities arise from both the illumination source and the imaging system. By correcting for the non-uniformities it is possible to make quantitative measurements of an electrophoresis gel, thus increasing the information which can be obtained from the electrophoretic analysis.

The non-uniformities due to the illumination source are characterized by sampling a portion of the source with a linear array detector. In order to sample the source, a mirror or beamsplitter is appropriately positioned, for example along the central optical axis of the electrophoresis apparatus. Preferably the mirror is brought into the sampling position with a stage whenever the source non-uniformities are to be measured. The reflected light is enlarged before it is measured with a linear detector.

Once a profile of the source has been determined, a correction file is stored within the memory of an associated data processor. Since the correction file must contain the same number of data points as the actual sample image file, a number of the correction data points must be filled-in by the system processor. These additional correction data points are determined through interpolation and by utilizing the source symmetry.

After a completed correction file has been stored, an image of the sample is taken and a corresponding image file stored within memory. To create a corrected image file, the initial sample image file is normalized with the correction file.

The non-uniformities due to the lens assembly are characterized by passing a secondary source of known uniformity through the lens assembly. If desired, the same mirror used to determine the source non-uniformities can be used to determine the lens non-uniformities. The secondary source is a linear source, either a continuous source or a series of point sources. As before, a correction file is created and stored which is used to normalize the image file.

A further understanding of the nature and advantages of the present invention may be realized by reference to the remaining portions of the specification and the drawings.

DESCRIPTION OF THE PREFERRED EMBODIMENT

Figure 1:
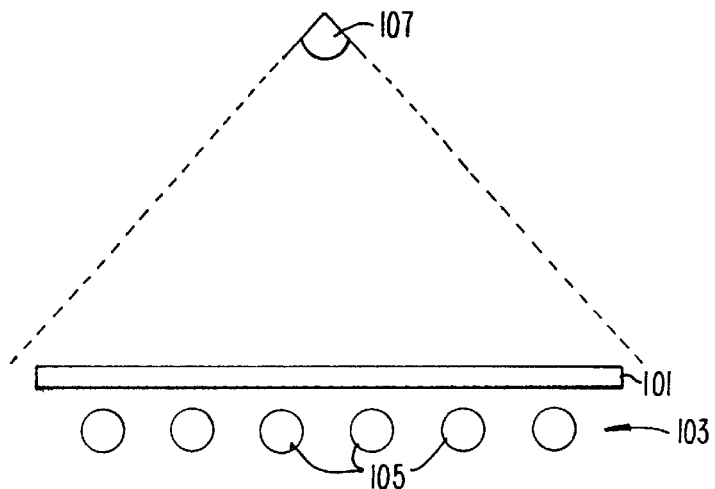
FIG. 1 is an illustration of a cross-section of a gel electrophoresis apparatus according to the prior art.

FIG. 1 is an illustration of a cross-section of a gel electrophoresis apparatus according to the prior art. In this system a gel plate 101 is illuminated by a light source 103. Light source 103 is comprised of a plurality of individual light bulbs 105. The light from source 103 causes fluorophores or other fluorescing material contained within specific areas of sample 101 to fluoresce. A detector 107 receives the fluorescence from sample 101 and uses this information to determine the areas of fluorescence on sample 101.

Although the intensity of the fluorescence from sample 101 contains additional information such as the quantity of the fluorescing material, to date the ability to quantify this information has been limited due to non-uniformities in the illumination source and the imaging optics.

The light intensity from an individual light bulb 105 is relatively uniform along the majority of the length of the bulb. At either end of the bulb the brightness level exhibits a minor fall-off in intensity. This fall-off can be minimized through the use of reflectors, masks, diffusion filters, or some combination thereof. The effects of fall-off can also be minimized by simply using longer bulbs. By extending the bulbs, the end portions of the bulbs exhibiting the lower brightness levels are located past the sampling area of the apparatus, thus placing only the relatively uniform length of the bulb under the sample.

Figure 2:
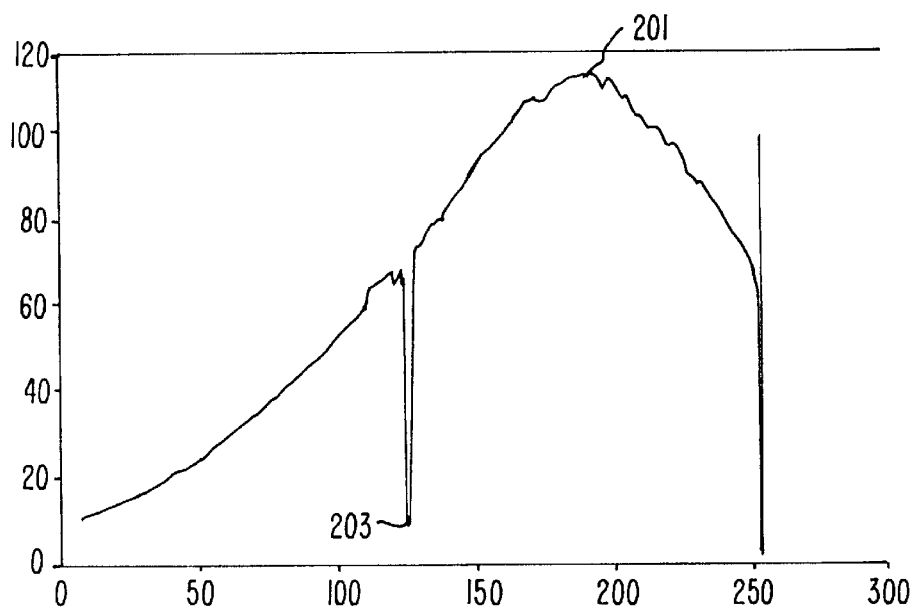
FIG. 2 is the intensity profile of a single light bulb measured perpendicular to the axis of the bulb.
Figure 3:
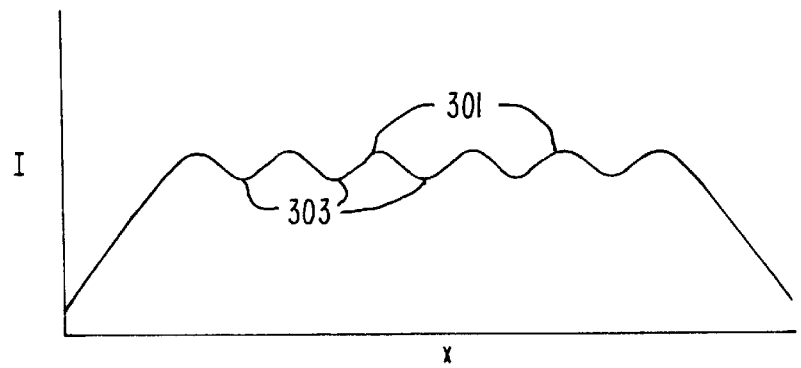
FIG. 3 is an illustration of an intensity profile for a source with multiple bulbs.

FIG. 2 is the intensity profile of a single light bulb 105 measured perpendicular to the axis of the bulb. As expected, the profile exhibits a peak 201 centered directly above the bulb with a rapid fall off in the intensity as the distance from the bulb is increased. A dip 203 is a result of a scribe mark on the stage. FIG. 3 is an illustration of an intensity profile for source 103 measured perpendicular to the axes of bulbs 105. Peaks 301 are located over the center lines of the individual bulbs 105 while valleys 303 represent the midpoints between bulbs. Further improvement in source uniformity can be achieved by increasing the number of bulbs and decreasing the separation between bulbs.

Figure 4:
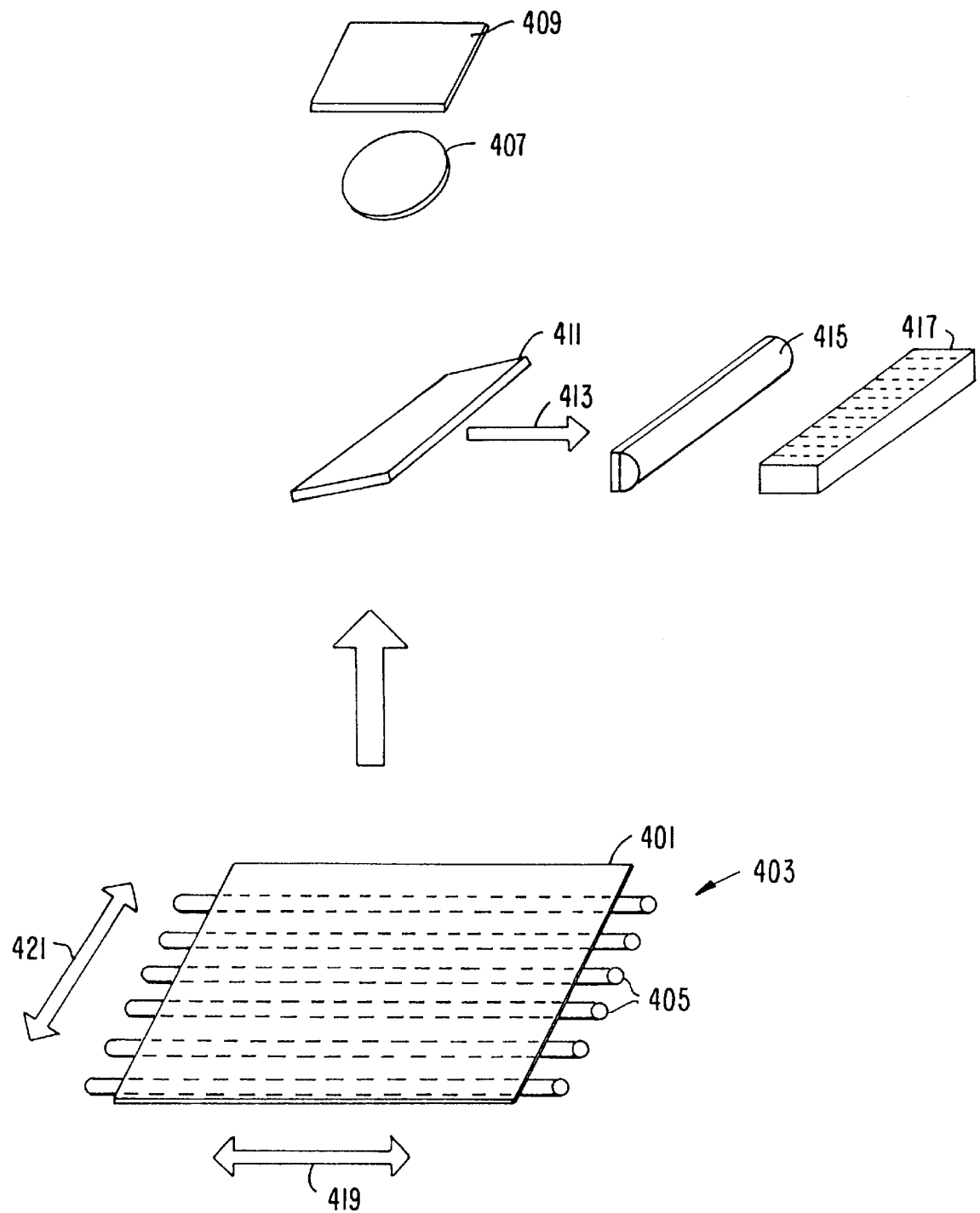
FIG. 4 is an illustration of an embodiment of the invention.

FIG. 4 is an illustration of an embodiment of the invention. A sample plane 401 is illuminated with a light source 403. In this embodiment light source 403 consists of a series of light bulbs 405 although the invention is equally applicable to other light sources. In normal usage a sample, for example an electrophoresis gel, would lie within sample plane 401. The fluorescence from the excited regions of such a sample would be imaged by a lens assembly 407 onto a detector 409. Preferably detector 409 is a two dimensional CCD array.

In order to remove the non-uniformities arising from illumination source 403, a mirror 411 is used to sample a portion of the source. In one embodiment of the invention, mirror 411 is coated with a partial reflector, thus allowing a portion of the light from source 403 to reach lens 407 and detector 409. In this embodiment a second portion of the light from source 403 is reflected along a path 413. Assuming that only a small portion of the light is reflected along path 413 by mirror 411, one of the principal benefits of this embodiment is that mirror 411 need not be removed during the normal operation of the system. However, in this configuration mirror 411 will introduce non-uniformities which also must be taken into account during the correction process. In an alternate embodiment, mirror 411 is coupled to a stage (not shown). During normal operation the stage moves mirror 411 out of the light path, insuring an unobstructed light path from a sample at plane 401 to imaging lens assembly 407. In order to determine the non-uniformities of light source 403, the stage moves mirror 411 into a sampling position such as that shown in FIG. 4.

In order to determine the non-uniformities of illumination source 403, mirror 411 reflects a portion of source 403 along path 413 through a lens 415. Lens 415 focuses the light onto a linear detector array 417. Preferably detector 417 is a linear CCD array. However, other forms of in-line detector arrays may be used. Furthermore it is not necessary that array 417 be continuous. Rather, array 417 may consist of a series of point detectors and the uniformity profile between point detectors interpolated from the measured points.

The dimensions and location of mirror 411, lens 415, and detector 417 are driven by the symmetry of source 403. For example, a source such as that shown in FIG. 4 can be expected to be relatively uniform along an axis 419 due to the illumination uniformity of extended bulbs 405 along their individual major axes. In contrast, source 403 can be expected to have an illumination profile similar to that illustrated in FIG. 3 along an axis 421. Therefore by measuring the profile of source 403 along axis 421 as shown, the non-uniformities of the entire source can be determined.

Figure 5:
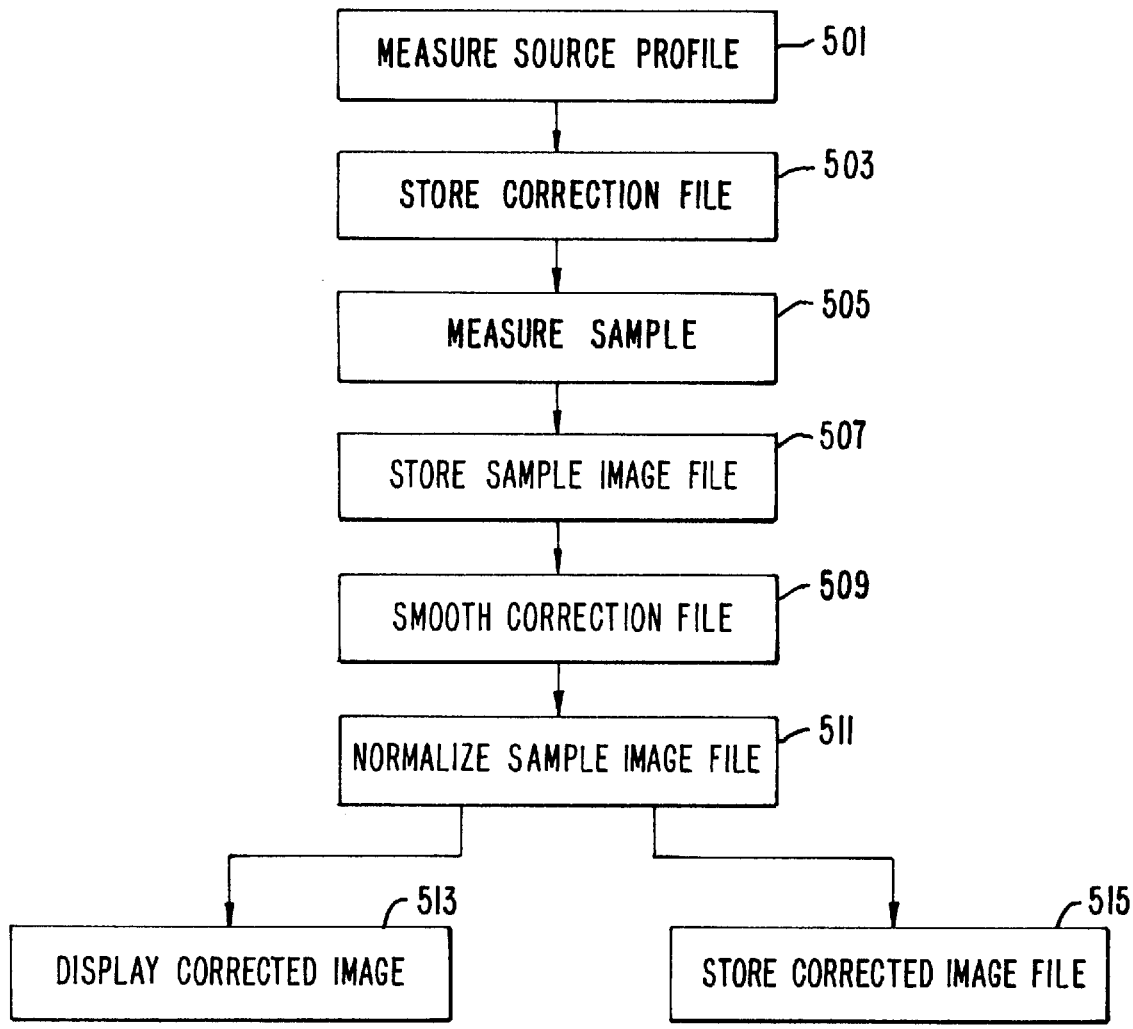
FIG. 5 is a block diagram outlining the principal steps used in correcting an image for illumination non-uniformities in accordance with the present invention.

Once the source non-uniformities have been determined the image of the sample may be corrected. FIG. 5 is a block diagram outlining the principal steps in correcting an image using the present invention. First, the profile of the source must be measured using the technique described above (step 501). Once the profile has been determined, a correction file is stored (step 503) within a memory associated with a system image processor.

Figure 6:
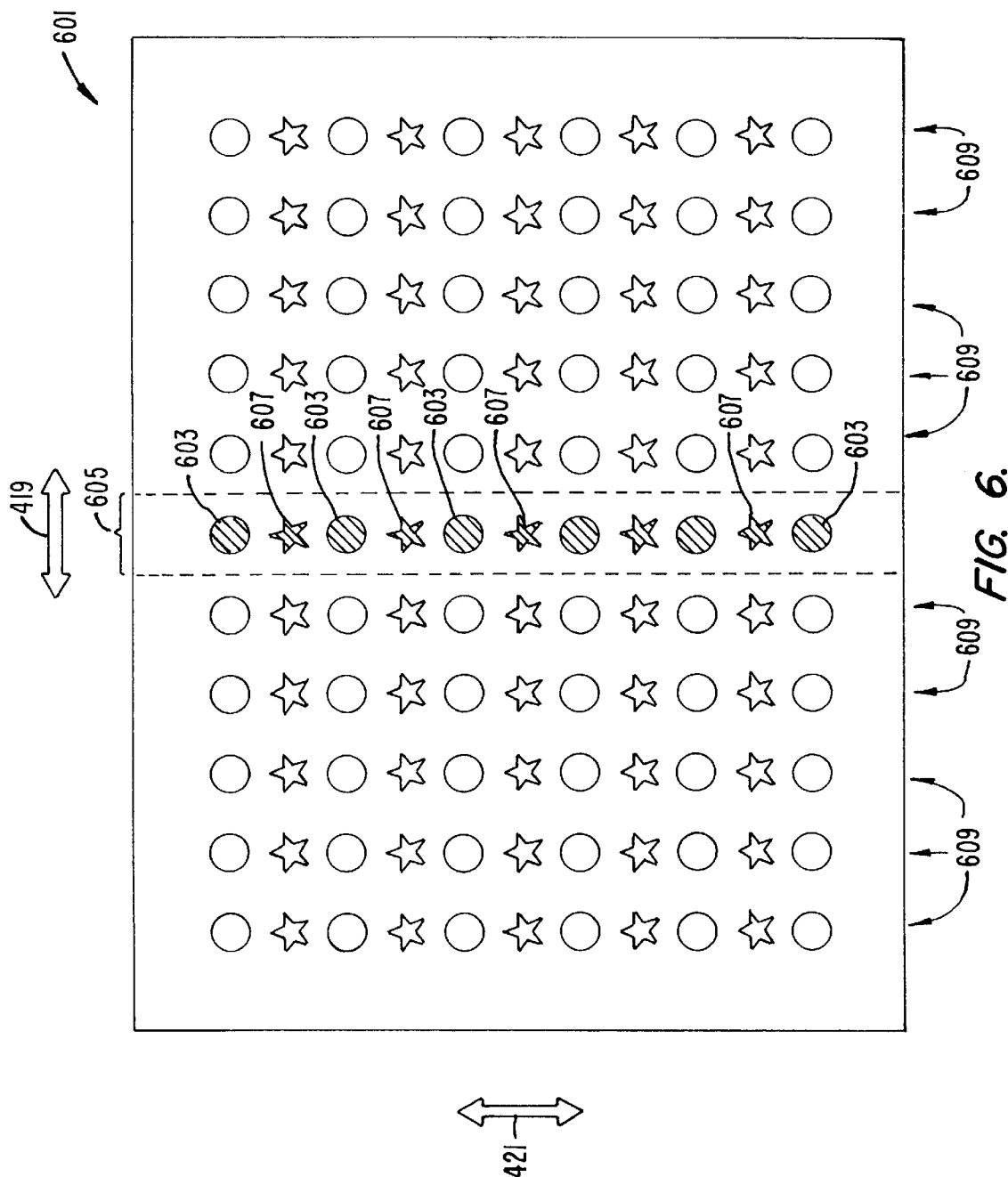
FIG. 6 illustrates the interpolation process used in preparing a correction file.

The correction file should contain the same number of correction data points as the number of points resulting from the sample imaging process. Since the number of correction data points are typically substantially less than the number of sample points, the correction data points must be filled-in by the processor. The filled-in correction data points take into account both the symmetry of the source and the number of pixels in detector 417. FIG. 6 illustrates the interpolation process. A matrix 601 represents a 11 by 11 matrix of correction data points, thus reproducing a sample image of 121 sample data points. Assuming a source such as that illustrated in FIG. 4 which is uniform along an axis 419 and non-uniform along an axis 421, most of the correction data points can be filled-in by the processor. In the illustrated example, correction data points 603 of column 605 were measured using the invention. Correction data points 607 of column 605 were filled-in through interpolation. Given the uniformity of the source along axis 419, remaining columns 609 are simply reproductions of column 605.

After the source profile has been measured, the sample image can be taken (step 505) and stored (step 507). Prior to normalizing the image, in the preferred embodiment the correction file is first smoothed (step 509) using a smoothing function such as those well known in the art. The smoothing function insures that any source of noise in the correction file is not amplified by the normalization process, resulting in a flawed, corrected sample image. Lastly, the sample file is normalized by dividing it by the correction file (or smoothed correction file if step 509 is applied) in order to achieve a corrected sample image file (step 511). The corrected sample image file can either be displayed (step 513) or stored (step 515) for later use.

Figure 7:
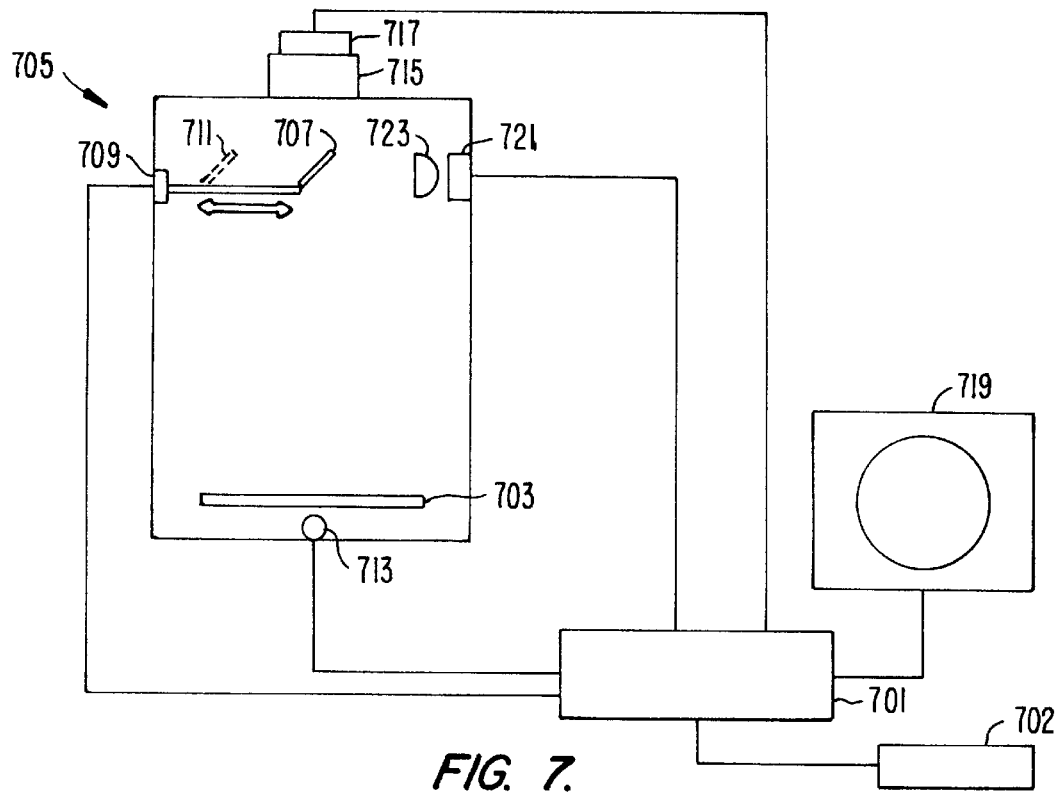
FIG. 7 is an illustration of the major components of a system according to the preferred embodiment of the invention.

FIG. 7 is an illustration of the major components of a system according to the preferred embodiment of the invention. In this embodiment the key system components are connected to a processor 701 which is connected to a user interface 702. Not only is processor 701 required for the interpolation/normalization processes to be performed in a timely fashion, but it also permits much of the process to be automated. In use, the sample image may be taken and stored either before or after the illumination source is profiled. Furthermore, it is not necessary to profile the source for every sample run since the source is relatively constant over short periods of time. Profiling the source for every sample run does, however, improve the correction accuracy. In the preferred embodiment the source is only periodically profiled, the new profile being compared to the last profile to determine if there have been any changes, for example changes due to the aging of a light bulb.

Assuming that the sample image is taken prior to the source profile, a sample 703 is first placed within electrophoresis apparatus 705. In this embodiment source profile mirror 707 is attached to a retractable stage 709. During the sample run stage 709 is retracted so that mirror 707 is in a location 711.

To take a sample image, a source 713 is turned on causing the appropriately marked regions of sample 703 to fluoresce. The fluorescence is imaged by a lens assembly 715 onto a detector 717. The sample image is stored as a sample file within a memory associated with processor 701. If desired, the sample image may be displayed on a monitor 719 prior to correction.

To take a source profile, sample 703 is removed from apparatus 705 and mirror 707 is moved into place with stage 709. Source 713 is turned on and a source profile is imaged onto a detector array 721 with a lens 723. If necessary, depending upon the symmetry of source 703, additional source profiles may be taken. For example, a second source profile could be taken along an axis perpendicular to the first by replicating mirror 707, lens 723, and detector 721 along the second axis. Once the source profile or profiles are taken, processor 701 can create a correction file and if desired, a smoothed correction file. This data is then used to normalize the image file as described above.

Figure 8:
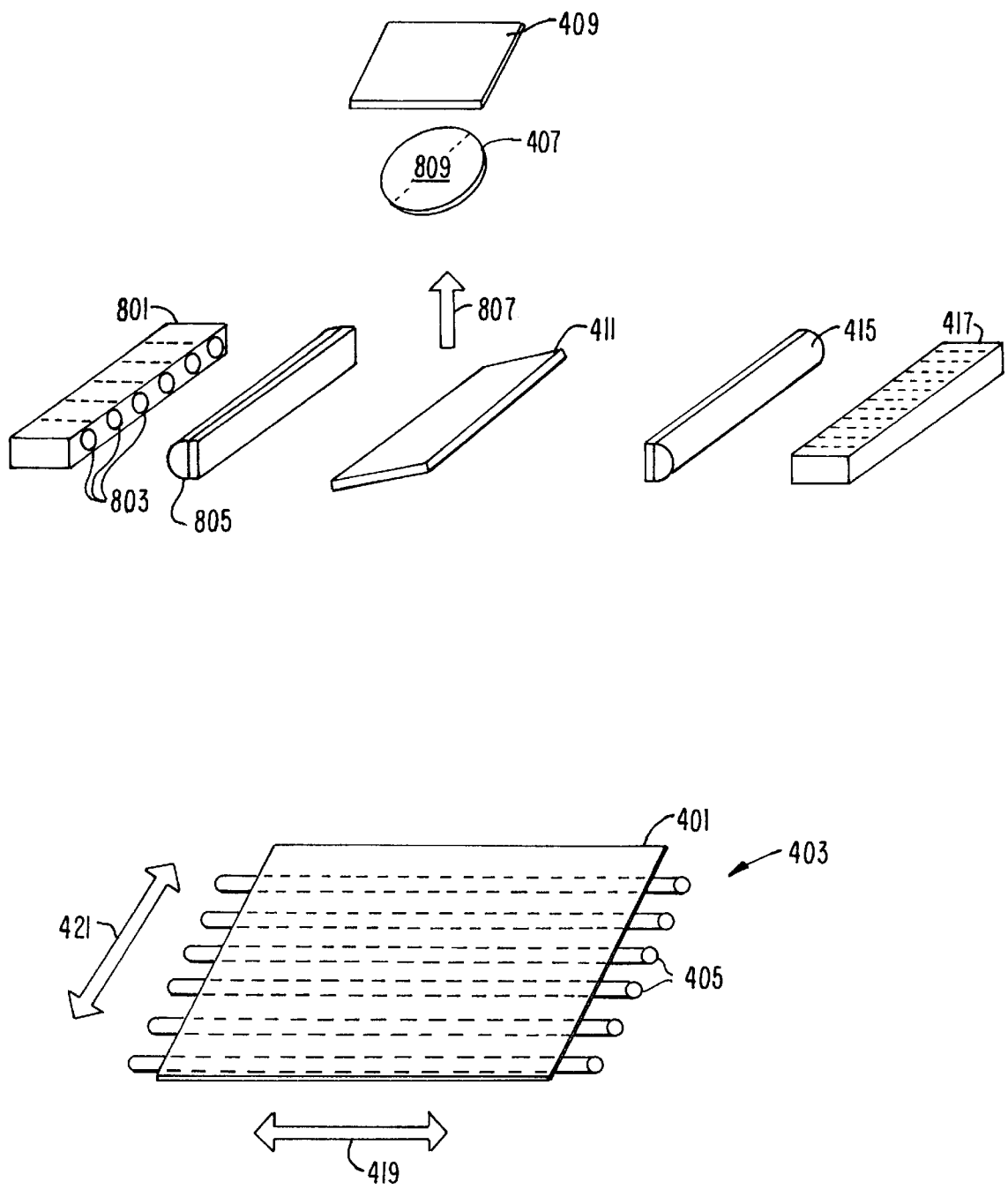
FIG. 8 is an illustration of an alternate embodiment of the invention which can be used to measure the non-uniformities of both the illumination source and the lens assembly.

In an alternate embodiment of the invention the source profiling mirror can be used to profile the lens assembly. This embodiment is illustrated in FIG. 8. This embodiment can be used in conjunction with the previously described embodiment in order to obtain a sample image corrected for both source and lens non-uniformities. If the source is a uniform source this embodiment can be used separately in order to correct for non-uniformities in the lens assembly alone. The source may be made uniform using a variety of techniques such as scanning sources, reflectors, and/or masks.

In order to remove non-uniformities due to lens assembly 407, a secondary source 801 is used. Source 801 is a line source, for example a series of light emitting diodes (LEDs) 803. Source 801 may also consist of a series of other types of point sources or a single line source such as a long light bulb. The radiation from source 801 is enlarged with a lens 805 before being reflected by mirror 411. As in the previous embodiment, mirror 411 may be a partial reflector thus allowing it to remain in place during the normal operation of the system. Mirror 411 may also be dedicated to the task of measuring lens and/or illumination source non-uniformities. If mirror 411 is a dedicated mirror, it is placed on a stage so that it can be moved out of the sample imaging path during normal system operation.

Mirror 411 reflects the radiation from source 801 along a path 807. The radiation then passes through lens assembly 407 onto detector 409. Assuming a uniform detector response (e.g., sensitivity) as is obtainable with a CCD array, and also assuming uniformity in mirror 411, lens 805, and source 801, any non-uniformity measured by detector 409 is due to lens assembly 407.

The apparatus illustrated in FIG. 8 assumes that lens assembly 407 exhibits a spherical symmetry, thus allowing the lens non-uniformities to only be determined along a single axis 809. If lens assembly 407 does not exhibit such symmetry, additional non-uniformity measurements must be made along other axes.

Once the lens non-uniformities have been determined, the sample image may be corrected following the same steps as outlined in FIG. 5. The only difference is that instead of measuring the profile of the source, step 501 is measuring the profile of lens assembly 407. The remaining steps such as creating a correction file and then using the correction file to normalize the sample file are the same as previously described.

Figure 9:
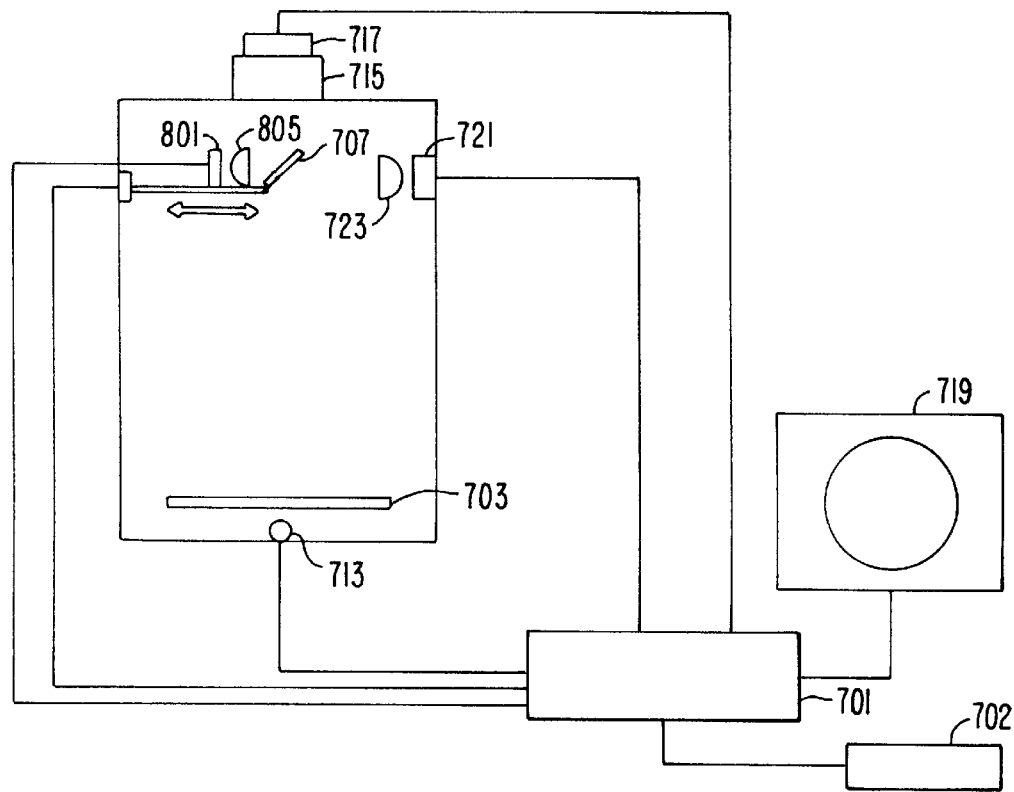
FIG. 9 is an illustration of a system according to the present invention which includes the components necessary to perform the lens non-uniformity measurements.

FIG. 9 is an illustration of a system according to the present invention which includes the components necessary to perform the lens non-uniformity measurements. This figure is identical to that shown in FIG. 7 with the addition of source 801 and lens 805. In this embodiment source 801 is connected to processor 701, thus allowing the lens non-uniformity measurement to be automated.

Figure 10:
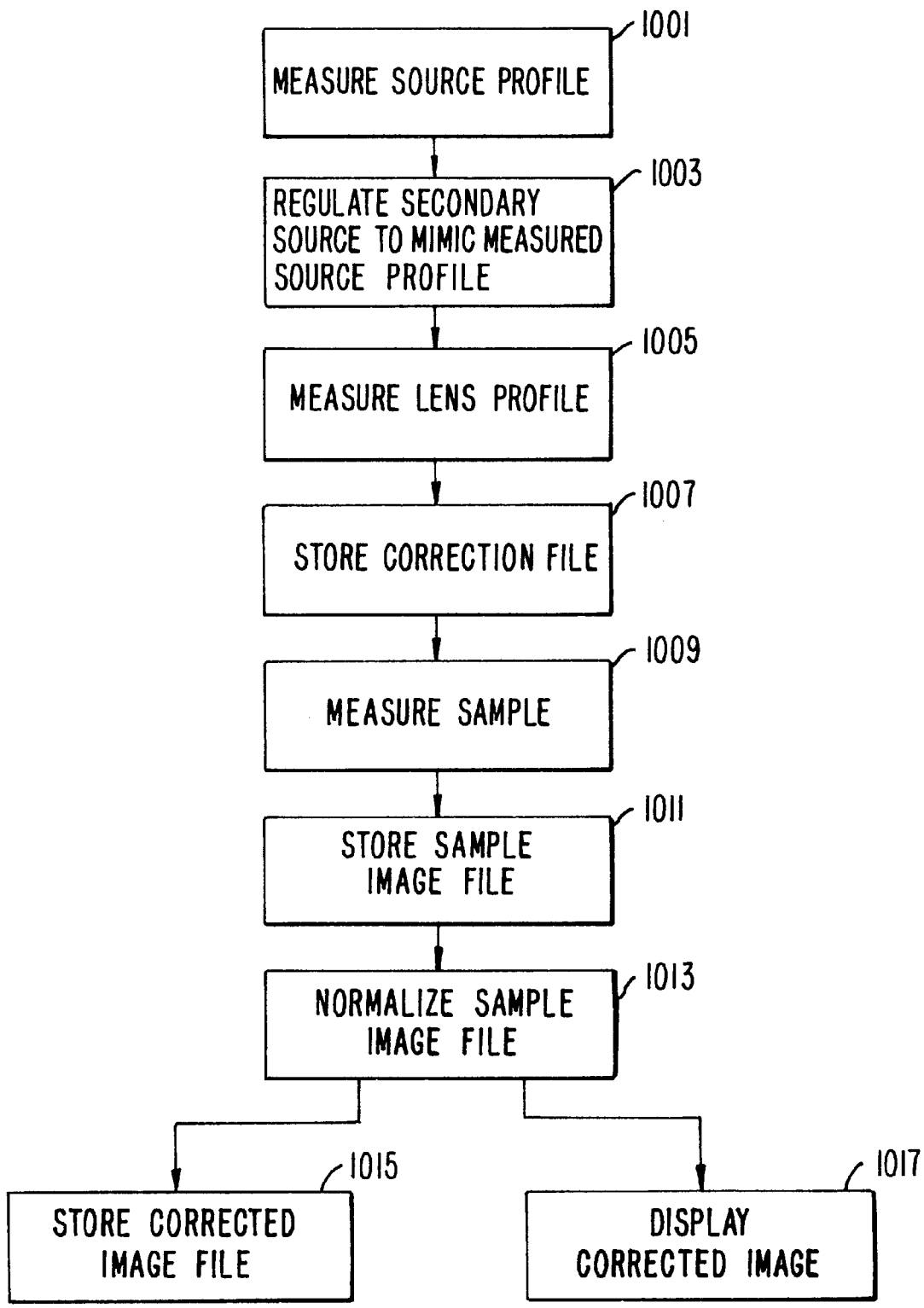
FIG. 10 is a block diagram outlining the principal steps used in accordance with another embodiment of the invention.

FIG. 10 is a block diagram outlining the principal steps used in accordance with another embodiment of the invention. In this embodiment the profile of the source is first determined using the system described above (step 1001). Once the source profile is determined, the profile of the secondary source can be altered to mimic the measured profile of the actual source (step 1003). This step requires that source 801 be comprised of a series of individually controllable point sources 803. Preferably point sources 803 are pre-calibrated and controlled by processor 701. Once the profile of secondary source 803 has been properly adjusted, a lens profile can be measured (step 1005) and a correction file stored (step 1007). Since source 801 has been regulated in order to provide the same profile as source 403, the stored correction file takes into account both the non-uniformities in illumination source 403 and the non-uniformities in lens assembly 407. As in the previous embodiments, the correction file must contain the same number of correction data points as the number of data points resulting from the sample imaging process. Thus the correction file contains a number of correction data points which are not measured, rather they are computed by processor 701 using a standard interpolation function.

After the correction profiles have been measured and an appropriate correction data file has been stored, the sample image is taken (step 1009), stored (step 1011), and normalized (step 1013). As in the previous embodiments, if necessary a smoothing function can be applied to the correction data file before it is used to normalize the sample image. Lastly the corrected sample file is either stored (step 1015) for later use, or immediately displayed (step 1017).

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

We claim:

1. An electrophoretic system comprising:

a platform including an electrophoresis gel holding region;

a light source providing illumination having a spatial intensity pattern, said illumination directed at said electrophoresis gel holding region along a first light path;

a first detector positioned in said first light path;

a first lens assembly interposed between said electrophoresis gel holding region and said first detector, said first lens assembly focussing light along said first light path onto said first detector;

a mirror located in said first light path, said mirror reflecting at least a portion of said light source illumination along a second light path and away from said first lens assembly;

a second detector positioned in said second light path, wherein said second detector outputs a plurality of signals representative of the non-uniformities of said light source;

a second lens assembly interposed between said mirror and said second detector, said second lens assembly focussing said light source illumination onto said second detector; and a processor coupled to said first and second detectors, wherein said processor receives said second detector output signals and normalizes an output of said first detector in response to said second detector output signals.

2. The electrophoretic system of claim 1, wherein said second detector is a linear detector array comprised of a plurality of individual detectors.

3. The electrophoretic system of claim 1, wherein said second detector is a linear CCD detector array.

4. The electrophoretic system of claim 1, further comprising a movable stage coupled to said mirror, wherein said stage has at least a first position and a second position, wherein said mirror reflects at least said portion of said light source illumination along said second light path and away from said first lens assembly when said stage is in said first position, and wherein said mirror is positioned outside of said first light path when said stage is in said second position.

5. The electrophoretic system of claim 1, wherein said mirror is a beamsplitter.

6. An electrophoretic system comprising:

a platform including an electrophoresis gel holding region;

a first light source providing illumination, said illumination directed at said electrophoresis gel holding region along a first light path;

a detector positioned in said first light path, wherein said detector outputs a plurality of signals representative of an incident intensity pattern;

a first lens assembly interposed between said electrophoresis gel holding region and said detector, said first lens assembly focussing light along said first light path onto said detector;

a second light source providing illumination along a second light path, said illumination from said second light source having a predetermined intensity pattern;

a mirror located in said first light path, said mirror reflecting illumination from said second light source through said first lens assembly onto said detector, wherein said intensity pattern of said second light source passing through said first lens assembly is measured by said detector; and a processor coupled to said detector, wherein said processor receives said detector output signals and determines the non-uniformities of said first lens assembly from said detector output signals.

7. The electrophoretic system of claim 6, wherein said second light source is a line source.

8. The electrophoretic system of claim 7, wherein said line source is comprised of a plurality of individual light sources.

9. The electrophoretic system of claim 6, further comprising a second lens assembly interposed between said second light source and said mirror.

10. The electrophoretic system of claim 9, wherein said second lens assembly is an image enlarger.

11. The electrophoretic system of claim 6, further comprising a movable stage coupled to said mirror, wherein said stage has at least a first position and a second position, wherein said mirror reflects illumination from said second light source through said first lens assembly onto said detector when said stage is in said first position, and wherein said mirror is positioned outside of said first light path when said stage is in said second position.

12. An electrophoretic system comprising:

a platform including an electrophoresis gel holding region;

a first light source providing illumination having an intensity pattern, said illumination directed at said electrophoresis gel holding region along a first light path;

a first detector positioned in said first light path, wherein said first detector outputs a plurality of signals representative of an incident intensity pattern;

a first lens assembly interposed between said electrophoresis gel holding region and said first detector, said first lens assembly focussing light along said first light path onto said first detector;

a second light source providing illumination along a second light path, said illumination from said second light source having a predetermined intensity pattern;

a mirror located in said first light path, said mirror reflecting at least a portion of said first light source illumination along a third light path and away from said first lens assembly, said mirror reflecting illumination from said second light source through said first lens assembly onto said first detector, wherein said intensity pattern of said second light source passing through said first lens assembly is measured by said first detector a second detector positioned in said third light path, wherein said second detector outputs a plurality of signals representative of said first light source intensity pattern;

a second lens assembly interposed between said mirror and said second detector, said second lens assembly focussing said first light source illumination onto said second detector; and a processor coupled to said first and second detectors, wherein said processor receives said first detector output signals and said second detector output signals and determines the non-uniformities of said first lens assembly from said first detector output signals and determines the non-uniformities of said first light source from said second detector output signals.

13. The electrophoretic system of claim 12, further comprising a movable stage coupled to said mirror, wherein said stage has at least a first position and a second position, wherein said mirror reflects at least said portion of said first light source illumination along said third light path and away from said first lens assembly when said stage is in said first position, wherein said mirror reflects illumination from said second light source through said first lens assembly onto said first detector when said stage is in said first position, wherein said mirror is positioned outside of said first light path when said said stage is in said second position.

14. The electrophoretic system of claim 12, wherein said second light source is comprised of a plurality of individual light sources, wherein an illumination intensity from each of said individual light sources is individually regulated by said processor, and wherein said processor regulates said individual light source intensities such that a second light source profile is substantially similar to said first light source profile.

15. A method of correcting an electrophoresis gel image comprising the steps of:

reflecting a portion of light from an electrophoresis gel illumination source onto a first detector array;

measuring a spatial intensity pattern with said first detector array for said electrophoresis gel illumination source;

determining an electrophoresis gel illumination source correction file from said measured spatial intensity pattern;

storing said electrophoresis gel illumination source correction file;

illuminating an electrophoresis gel with said electrophoresis gel illumination source, wherein at least one labeled region of said illuminated gel fluoresces;

imaging said illuminated electrophoresis gel onto a second detector array;

storing an electrophoresis gel image file;

normalizing said electrophoresis gel image file with said electrophoresis gel illumination source correction file; and storing said normalized electrophoresis gel image file.

16. The method of claim 15, further comprising the step of displaying said normalized electrophoresis gel image file.

17. The method of claim 15, wherein said reflecting step is further comprised of the step of reducing said reflected portion of light before said light strikes said first detector array.

18. The method of claim 15, further comprising the steps of:

translating a mirror into a first position, wherein said mirror in said first position performs said reflecting step; and translating said mirror into a second position, wherein said mirror in said second position allows said electrophoresis gel to be unobstructively illuminated by said electrophoresis gel illumination source.

19. A method of correcting an electrophoresis gel image comprising the steps of:

reflecting a portion of light from a first light source array through a first lens assembly onto a detector array;

measuring an intensity pattern with said detector array of said first light source array;

determining a first lens assembly correction file from said measured intensity pattern;

storing said first lens assembly correction file;

illuminating an electrophoresis gel with an electrophoresis gel illumination source, wherein at least one labeled region of said illuminated gel fluoresces;

imaging said illuminated electrophoresis gel onto said detector array;

storing an electrophoresis gel image file;

normalizing said electrophoresis gel image file with said first lens assembly correction file; and storing said normalized electrophoresis gel image file.

20. The method of claim 19, further comprising the step of displaying said normalized electrophoresis gel image file.

21. The method of claim 19, further comprising the step of enlarging said portion of light from said first light source array with a second lens assembly before said reflecting step.

22. The method of claim 19, further comprising the steps of:

translating a mirror into a first position, wherein said mirror in said first position performs said reflecting step; and translating said mirror into a second position, wherein said mirror in said second position allows said electrophoresis gel to be unobstructively illuminated by said electrophoresis gel illumination source.

* * * * *